United States Patent [19]

LoPiano

[11] 4,328,799
[45] May 11, 1982

[54] SACRAL TOPICAL HYPERBARIC OXYGEN CHAMBERS

[76] Inventor: Rocco W. LoPiano, 26 Journal Square, Jersey City, N.J. 07306

[21] Appl. No.: 159,125

[22] Filed: Jun. 13, 1980

[51] Int. Cl.³ ............................................. A61M 35/00
[52] U.S. Cl. ........................... 128/207.26; 128/205.26; 128/202.12; 128/299; 128/300; 269/322; 269/328
[58] Field of Search .................. 128/202.12, 207.26, 128/30, 30.2, 205.26, 297, 298, 299, 300, 206.24, 206.26, 206.27, 200.24, 33, 325, 20, 133, 134, 31, 37, 38, 44; 5/503; 269/322, 328

[56] References Cited

U.S. PATENT DOCUMENTS

| | | | |
|---|---|---|---|
| 2,098,272 | 11/1937 | Benson | 128/299 |
| 2,287,939 | 6/1942 | Kraft | 128/30.2 |
| 2,314,955 | 3/1943 | Slater | 128/30 |
| 2,418,473 | 4/1947 | Lambertsen et al. | 128/205.26 |
| 2,625,155 | 1/1953 | Engelder | 128/206.24 |
| 3,062,215 | 11/1962 | Heyns | 128/30 |
| 3,638,973 | 2/1972 | Poletti | 128/20 |
| 3,669,118 | 6/1972 | Colon-Norales | 128/361 |
| 3,850,168 | 11/1974 | Ferguson et al. | 128/206.27 |

FOREIGN PATENT DOCUMENTS

| | | | |
|---|---|---|---|
| 26953 | of 1903 | United Kingdom | 128/298 |
| 837250 | 6/1960 | United Kingdom | 128/206.24 |

Primary Examiner—Henry J. Recla
Attorney, Agent, or Firm—DeLio and Libert

[57] ABSTRACT

A hyperbaric oxygen treatment apparatus for use by a patient recumbent on a bed comprising, an openface chamber and an adjustable rigid support therefore, the chamber having a closed rear side and an open front side, the opening in the front side of the chamber being defined by a forwardly projecting first gasket presenting a resilient feather edge which is adapted for substantially gas-tight engagement with a human body surface along a line surrounding an area to be treated, and the rear side of the chamber being provided with fittings for connection to the support and to a controlled source of oxygen, and the rigid support including articulated members connecting the chamber to at least one bed rail.

2 Claims, 11 Drawing Figures

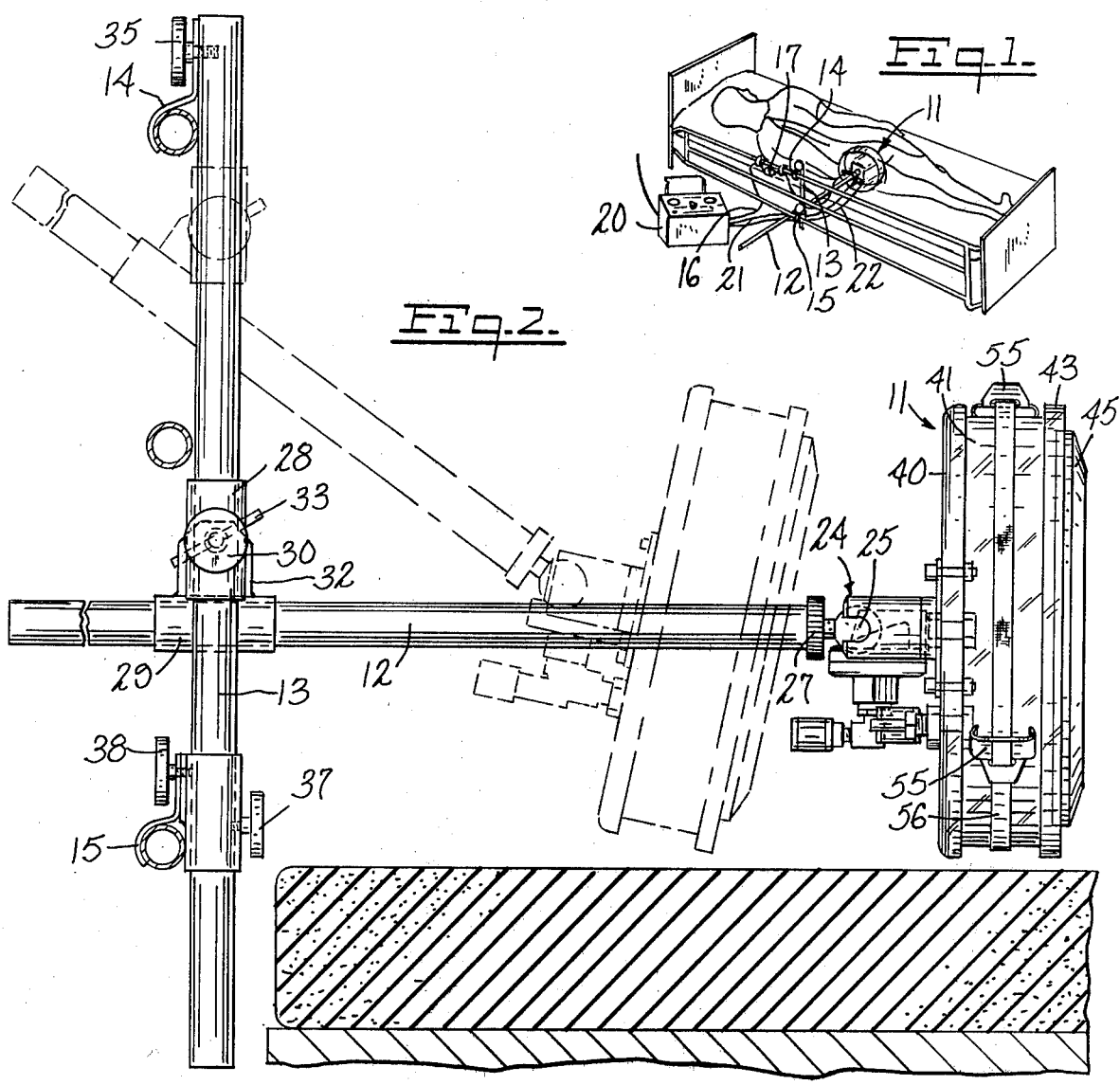
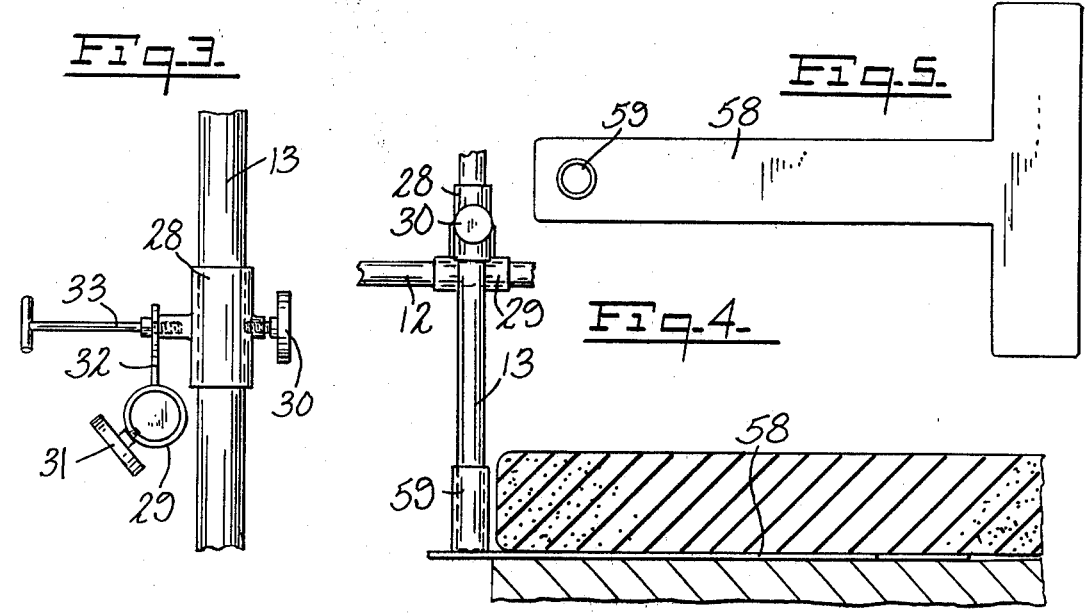

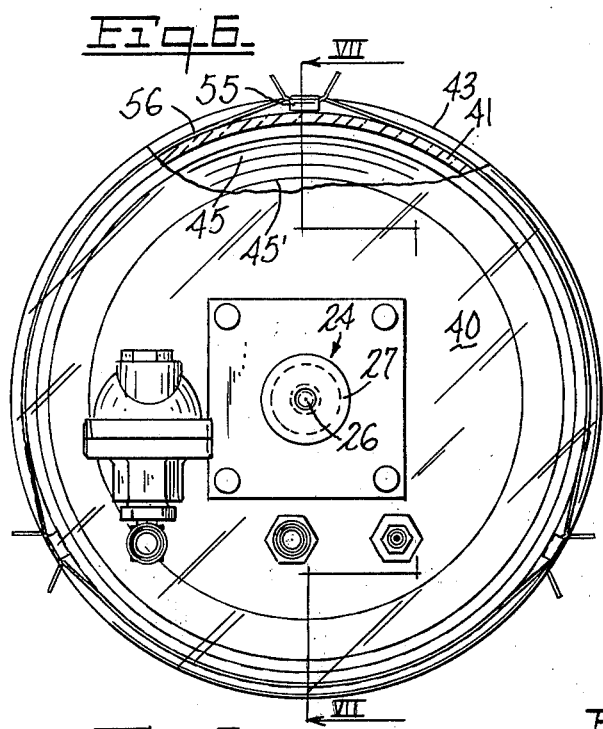
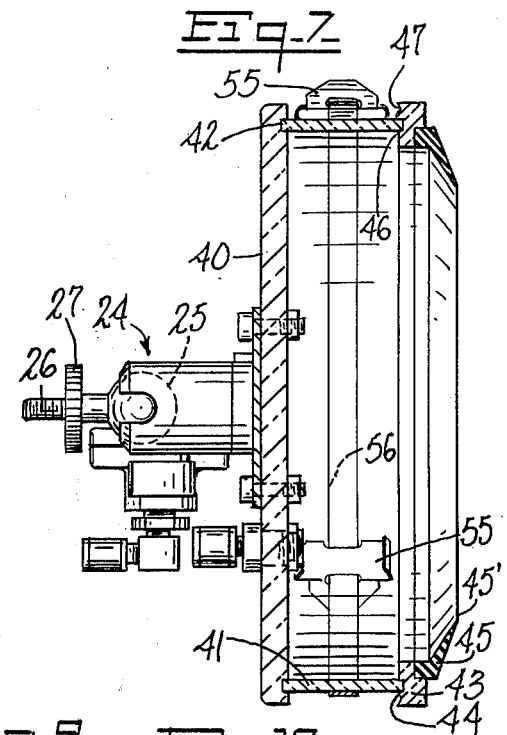
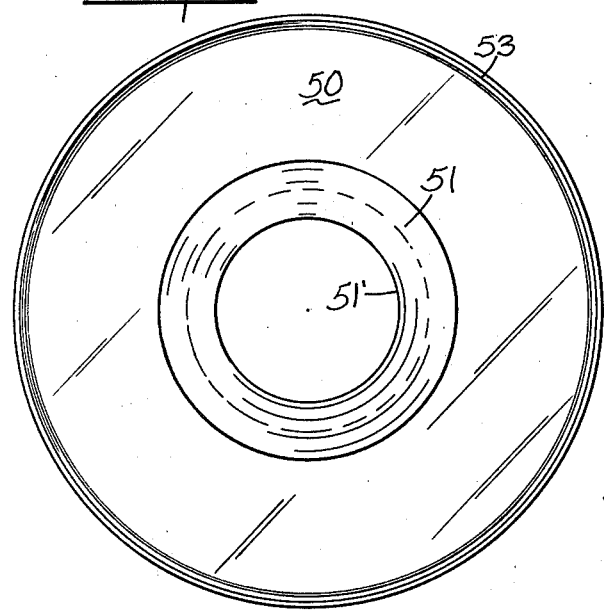
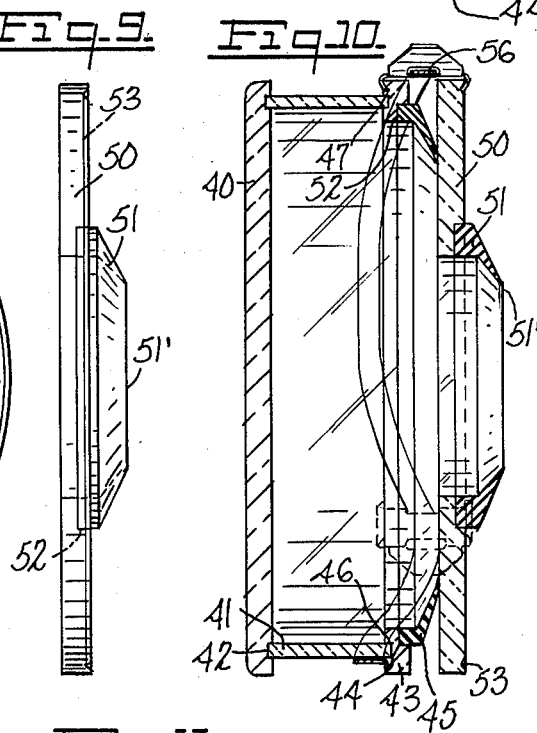
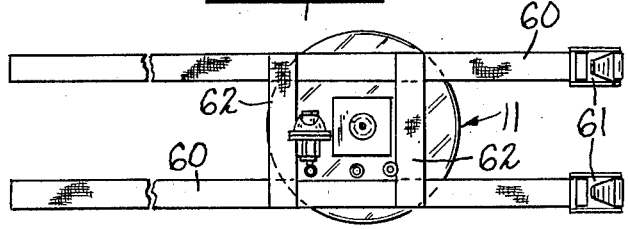

SACRAL TOPICAL HYPERBARIC OXYGEN CHAMBERS

This invention relates to a controlled pressure oxygen treatment system which includes an open-walled chamber adapted to be applied to a portion of the surface area of a human body, normally including part of the trunk, so that said body area closes the chamber, and a gas (oxygen) supply circuit, with controls, adapted to supply gas to the chamber automatically in pulses of predetermined frequency, duration and pressure.

It is known to use hyperbaric oxygen topically to treat pressure sores, wounds, skin lesions, decubiti and ulcers, chambers for this purpose being shown and described in Fischer U.S. Pat. Nos. 3,744,491, July 10, 1973 and 4,003,371, Jan. 18, 1977. In these chambers, the flow of oxygen past the enclosed leg or arm of a patient is continuous, at a low constant pressure of 22 mmHg, for example, and is continued for several hours a day (preferably six to eight) over periods which may average several weeks, to aid in the healing of various lesions.

Studies have now revealed that the treatment time for ulcerations and lesions originating from various etiologies can be substantially reduced by resorting to the use of pulsating oxygen treatment, as in the oxygen chamber disclosed in applicant's copending application Ser. No. 06/052,488, filed June 27, 1979. Actual trials of that system in a leading hospital have shown a median healing time of 19 days, substantially less than the time required for more conventional treatment.

It is accordingly an object of the present invention to provide a treatment chamber for a portion of a human body specially adapted for use with a pulsed oxygen supply. Suitable oxygen supply circuits are disclosed in Fischer Applications Ser. No. 858,960 (now abandoned) and its C.I.P., Ser. No. 06/052,488, filed June 27, 1979.

It is another object of the invention to provide such a chamber which is designed to use the hospital oxygen supply, to which it can be connected and from which it can be removed in seconds.

It is a further object of the invention to provide a chamber which is of simple construction, sturdy and easily cold-steralized.

It is another object of the invention to provide an open-walled chamber which is adapted to be applied extracorporeally to the ulcerated body, the surface of which completes the closure of the chamber.

It is a still further object of the invention to provide such a chamber with readily interchangeable windows, varying in size, to accommodate lesions of different sizes without overexposure of healthy areas to the oxygen.

It is yet another object of the invention to provide certain improvements in the form, construction and arrangement of the several parts wherey the above-named and other objects of the invention can readily be achieved.

The invention accordingly comprises the features of construction, combination of elements and arrangement of parts which will be exemplified in the construction hereinafter set forth, and the scope of the invention will be indicated in the claims.

A practical embodiment of the invention is shown in the accompanying drawings wherein:

FIG. 1 represents a somewhat diagrammatic perspective view of the chamber as applied to a patient;

FIG. 2 represents a side elevation of the chamber and its supporting elements in use;

FIG. 3 represents a detail elevation of the adjustable joint between the chamber stem and its bed stand;

FIG. 4 represents a detail elevation of the bed stand mounting, as used in the absence of a bed rail;

FIG. 5 represents a detail plan view of the bed stand support plate used in FIG. 4;

FIG. 6 represents an elevational view of the back of the chamber, part of the housing being broken away to show the attachment of a retaining clip;

FIG. 7 represents a vertical section on the line VII—VII of FIG. 6;

FIG. 8 represents an elevation of an auxiliary ring having a smaller opening;

FIG. 9 represents an edge view of the ring shown in FIG. 8;

FIG. 10 represents a vertical section like FIG. 7, showing the superposition of a ring having a smaller lumen over the basic large built-in ring; and FIG. 11 represents a plan view of a double support belt, associated with the oxygen chamber.

Referring to the drawings, the manner of use of the chamber in treatment of a sacral lesion is illustrated in FIG. 1 wherein the patient is shown lying on her left side with the sacral area in a substantially vertical position. The oxygen chamber, shown generally at 11, is held in operative position against the area to be treated by means of the chamber support stem 12, adjustably fixed on the bed stand 13 which, in turn, is supported on upper and lower bed rails by the adjustable upper and lower hooks 14, 15. A gas (such as $O_2$) is supplied to the chamber by a tube 16 which may be provided with an in-line humidifier 17 and is connected to the control box 20. A second tube 21 connects the interior of the chamber with a pressure sensing instrument (not shown) in the control box 20, and the third tube 22 is the oxygen relief tube.

The control box 20 may suitably correspond to the control apparatus 72 shown in FIGS. 8 and 9 of the copending application of Fischer, Ser. No. 06/052,488, under which the owner of the present application is licensed, said apparatus being adapted to supply a pulsed flow of oxygen to a treatment chamber at controlled rates and pressures, as explained below.

The support arm 12 is coupled centrally to the back of the chamber by a releasable and adjustable ball and socket joint 24, the ball element 25 being mounted on a screw 26 having a knurled head 27, by means of which the screw can readily be engaged with and disengaged from the internally threaded forward end of the stem 12. The engagement of the stem with the bed stand 13 is effected by means of a fitting which includes a collar 28 rotatable and slidable on the bed stand 13, a stem support bracket 29, the collar and bracket each having a set screw 30, 31, respectively, and a bracket hanger 32 with its adjusting screw 33. This fitting makes possible universal adjustment of the support stem 12 in relation to the bed stand 13.

The upper hook is engaged with the upper end of the bed stand 13 by means of a screw 35, the hook being shaped to engage a bed rail firmly when the screw is tightened. The lower hook 15 is mounted on the stand 13 by means of a sleeve 36, an adjusting screw 37 and a hook tightening screw 38 which holds the hook in tight engagement with a lower bed rail. The lower hook is shown in FIGS. 1 and 2 as being directed downwardly, to engage the bed rail from above, but its orientation can be reversed if desired by reversing the position of the sleeve 36 on the bed stand.

The oxygen chamber 11 comprises a flat, circular rear wall 40, an annular wall 41 having one edge set in a groove 42 adjacent to the periphery of the rear wall, and an annular rim 43, rabbetted at 44 to receive the thickened base of a resilient sealing gasket 45. The feather edge 45' of the gasket defines the opening of the chamber which is to be closed by contact with the area of the patient's body containing a lesion or the like to be treated, and this edge, therefore, projects a plane farthest from all other parts of the chamber. The rim 43 is grooved at 46 to receive the front edge of the wall 41 and has an additional annular groove 47, radially outward from the groove 46, for a purpose described below.

The rear wall 40 is provided with male or female fittings to engage tightly with the complementary fittings on the tubes 16, 21 and 22, to provide operative connection of the chamber to the control box 20.

The opening defined by the edge 45' of the gasket corresponds to the maximum body surface area which can be treated. It is known, however, that the smallest size opening possible gives the best results as long as there is no direct contact of the gasket with the wound to be treated. The apparatus therefore includes one or more (preferably two) auxiliary rings, as shown in FIG. 9, each having a flat annular plate 50 and a tapered gasket 51 set in a rabbet 52 around its central opening. The feather edge 51' defines a much smaller opening than the edge 45' and can be advantageously used on smaller wounds. The manner of use of the separate rings is illustrated in FIG. 10 where the plate 50 is applied to the front of the gasket 45 and is held there forcefully by the engagement of spring clips 55 which are carried on an elastic belt 56, resting normally around the periphery of the wall 41 (FIG. 7), but available to be snapped into the groove 47 and a complementary groove 53 in the face of the plate 50 (FIG. 10) adjacent to its peripheral edge, when an auxiliary ring is used.

The fixed rim 43 and auxiliary ring 50, with their gaskets 45 and 51, respectively, are shown as being annular in form, but it will be understood that other forms such as oval, square or elongated could be used in special situations, if desired.

If the patient is to be treated in a bed without side rails, the bed stand 13 can be supported very firmly by means of the under mattress plate 58 which is T-shaped in plan view (FIG. 5) and has an integral upstanding socket 59 at its "stem" end to receive the lower end of the stand. The mattresses normally used on beds adapted for therapeutic treatments are normally very firm and the shape of the plate is such that its tendency to tilt in any direction is negligible.

While it is possible for a patient to remain immobile in a position such that a lesion on the like is retained within the opening of a gasket 45 or 51 and with the body surface in sealing contact therewith, greater security can be provided by the use of a support belt such as that shown in FIG. 11. The belt has two straps 60 with buckles 61 and a pair of cross-straps 62 which leave a square opening of a size to receive the various tube terminals and chamber mounting means which are located on the rear wall 40. The chamber is placed carefully in its desired position on the patient's body and the straps 60 are buckled around the body just tightly enough to hold the chamber in place.

The oxygen chamber operates as determined by the apparatus in the control box 20, on the principle of pulsed pressure, consisting of a compression phase followed by a quick decompression phase. The control apparatus is connected to a standard unrestricted 50 psi oxygen source and is set, preferably, to operate with a 10-second compression phase (from 0 mmHg to 40 mmHg) followed by a one-second decompression phase (from 40 mmHg to 0 mmHg). If desired, the upper figure can be varied below 40 mmHg but the compression phase should not be operated below 22 mmHg. The humidification of the chamber, by means of humidifier 17, should achieve at least 50% relative humidity.

The recommended treatment time usually consists of two sessions per day, each lasting one hour, unless the physician orders otherwise. Treatment with this controlled pressure oxygen delivery system is not a substitute for proper primary treatment of the basic disorder and proper nursing care, but can be a valuable adjunct to the standard medical and/or surgical management of the patient.

It will thus be seen that the objects set forth above and those made apparent from the preceding description are efficiently attained and, since certain changes may be made in the construction shown an described without departing from the spirit and scope of the invention, it is intended that all matter contained in the above description or shown in the drawings shall be interpreted as illustrative and not in a limiting sense.

What I claim is:

1. A hyperbaric oxygen treatment apparatus for use by a patient recumbent on a bed comprising, an open-faced chamber and an adjustable rigid support therefore, the chamber having a closed rear side and an open front side, the opening in the front side of the chamber being defined by a forwardly projecting first gasket presenting a resilient feather edge which is adapted for substantially gas-tight engagement with a human body surface along a line surrounding an area to be treated, and the rear side of the chamber being provided with fittings for connection to the support and to a controlled source of oxygen, and the rigid support including articulated members connecting the chamber to at least one bed rail.

2. A hyperbaric oxygen treatment apparatus comprising, an open-faced chamber and an adjustable rigid support including articulated members connecting the chamber to at least one bed rail, the chamber having a substantially circular closed rear side and an open front side, the opening in the front side of the chamber being defined by a forwardly projecting annular first gasket presenting a resilient feather edge which is adapted for substantially gas-tight engagement with a generally planar human body surface along a line surrounding an area to be treated, and the rear side of the chamber being provided with fittings for connection to a controlled source of a treatment gas, the first gasket being of substantially the maximum size permitted by the diameter of the chamber, the apparatus including a mounting ring and second gasket fixed in said ring and presenting a resilient feather edge which defines an opening in the mounting ring smaller than the opening defined by the first gasket, and means for holding the mounting ring of the second gasket tightly against the feather edge of the first gasket, said holding means comprising a plurality of spring clips.

* * * * *